United States Patent [19]

Bennewitz et al.

[11] 4,379,406
[45] Apr. 12, 1983

[54] RELATIVE HUMIDITY DETECTOR SYSTEMS AND METHOD OF INCREASING THE CALIBRATION PERIOD OF RELATIVE HUMIDITY DETECTOR SYSTEMS

[76] Inventors: Paul F. Bennewitz, 8310 Cutler Ave., Albuquerque, N. Mex. 87110; Matt C. Bennewitz, 905 Nakomis Ct., NE., Albuquerque, N. Mex. 87112

[21] Appl. No.: 190,734

[22] Filed: Sep. 25, 1980

[51] Int. Cl.³ .......................................... G01N 25/56
[52] U.S. Cl. .............................. 73/336.5; 324/65 R; 338/35
[58] Field of Search ...................... 73/336.5, 336, 335; 338/35, 34; 324/65 R

[56] References Cited

U.S. PATENT DOCUMENTS

| | | | |
|---|---|---|---|
| 3,196,682 | 7/1965 | Johnson, Jr. | 324/65 R |
| 3,696,360 | 10/1972 | Gajewski | 73/336.5 |
| 4,143,177 | 3/1979 | Kovac et al. | 324/61 R |
| 4,261,179 | 4/1981 | Dageford | 73/336.5 |
| 4,270,085 | 5/1981 | Terada et al. | 73/336.5 |
| 4,288,775 | 9/1981 | Bennewitz et al. | 338/35 |

*Primary Examiner*—Donald O. Woodiel

*Attorney, Agent, or Firm*—William W. Cochran, II

[57] ABSTRACT

Sensor and method of fabricating a sensor for detecting relative humidity with a substantially linear response from 0% to 100% and also detecting temperature. The sensor utilizes a unique essentially pure $Al_2O_3$ layer which has a disordered crystalline structure and a density gradient which varies from a low density at its lower surface to a higher density at its upper surface which together produce the desired linear response to relative humidity.

The sensor is employed as a three-terminal semiconducting device which is biased with d.c. current, allowing implementation with standard ICs and LSI circuitry. Application of a biasing current on the top electrode allows the RH sensor to be operated simultaneously as a temperature sensor.

Also disclosed is a relative humidity detector system for adjusting sensitivity of the sensor for changes in environmental temperature so as to provide a true linear relative humidity response. Periodic discharge of the d.c. biasing signal increases an already long calibration period. Additionally, use of a constant resistance biasing circuit further extends the calibration period.

11 Claims, 20 Drawing Figures

RELATIVE HUMIDITY DETECTOR SYSTEMS AND METHOD OF INCREASING THE CALIBRATION PERIOD OF RELATIVE HUMIDITY DETECTOR SYSTEMS

BACKGROUND OF THE INVENTION

The present invention pertains generally to Humidity Sensors and more particularly to relative humidity detector systems and methods for increasing the calibration periods of relative humidity detector systems. Conventional humidity sensors utilize an aluminum layer which is partially anodized on its upper surface prior to deposition of the top electrode. The upper electrode is sufficiently thin to allow passage of water molecules to the partially anodized aluminum layer. The partially anodized aluminum layer changes resistance and capacitance when employed in a conventional ac stabilization circuit.

Although conventional humidity sensors have been developed to provide good response, slow anodization of the aluminum base material causes progressive impedance and capacitive change in the sensor due to exposure to moisture and residual acid remaining in the $Al_2O_3$ layer after the initial anodization process, especially when subjected to an ac current as utilized in conventional humidity sensor circuitry. As a result, the humidity detecting circuitry must be continually adjusted for proper operation throughout the life of the device. Even more seriously, use of the device in high temperature environments causes rapid aging even though appreciable amounts of moisture may not be present.

Attempts to overcome these problems by methods such as pre-aging the sensor, as disclosed in the prior art, have had limited success due to the non-transient nature of the slow anodization process.

Another attempt to overcome these problems is disclosed in U.S. Pat. No. 4,143,177 issued Mar. 6, 1979 to Kovac et al wherein a substantial portion of the Al metal present in the Al layer is removed by anodizing the Al layer using conventional anodization methods. As set forth, this process is used in an attempt to provide high temperature stability of the absolute humidity sensor disclosed by Kovac et al since a major portion of the Al metal left in the sensor which can become oxidized during operation or storage of high temperatures, is removed, which would otherwise affect the sensitivity and, consequently, calibration of the sensor.

However, since the $Al_2O_3$ layer of the Kovac et al sensor is formed according to conventional anodizing methods, the Kovac et al humidity detector is incapable of providing a linear response with respect to relative humidity. Rather, the Kovac et al detector can only provide a non-liner response to absolute humidity due to the structure and density of the $Al_2O_3$ layer resulting from the manner in which the $Al_2O_3$ is produced, i.e., with conventional anodizing methods. Furthermore, conventional methods of anodizing utilized by Kovac et al cannot remove essentially all the Al metal and other impurities in the $Al_2O_3$ layer, but only a substantial portion, as set forth in U.S. Pat. No. 4,143,177. Moreover, the Kovac et al device utilizes an external source to heat the substrate of the Kovac et al sensor for the purpose of driving moisture out of his sensor to prevent aging. This results, however, in an extremely slow response time of the Kovac et al sensor to changes in relative humidity.

Implementation of the sensor in the manner disclosed in application Ser. No. 92,766 entitled Device and Method of Manufacturing a Relative Humidity Sensor and Temperature Sensor filed Nov. 9, 1979 by Paul F. Bennewitz et al, now U.S. Pat. No. 4,288,755 has resulted in a detected response signal from said relative humidity sensor which varies slightly with changes in environmental temperature due to changes in output sensitivity of the sensor for changing environmental temperatures. Additionally, implementation of the sensor in high temperature environments, i.e. 50° C. or more, causes slow top electrode resistance changes which decreases the calibration period of the relative humidity detector system. The calibration period is also decreased by the application of a constant d.c. biasing signal.

SUMMARY OF THE INVENTION

The present invention overcomes the disadvantages and limitations of the prior art by providing improved relative humidity detector systems and improved methods of increasing the calibration period of relative humidity detector systems.

To achieve the foregoing in accordance with the purposes of the present invention, as embodied and broadly disclosed herein, the present invention may comprise a relative humidity detector system for lengthening the calibration period of a relative humidity sensor comprising a relative humidity sensor formed from an essentially pure layer of $Al_2O_3$ having a variable density gradient between a top and bottom electrode and means for biasing said top electrode with a predetermined d.c. current and voltage which remains substantially constant, whereby output sensitivity of said relative humidity sensor is maintained substantially constant by maintaining the predetermined current and voltage substantially constant.

The present invention may also comprise, in accordance with its objects and purposes, a relative humidity detector system for generating an output signal which varies linearly with relative humidity, independent of changes in surrounding environmental temperature, comprising: means for detecting surrounding environmental temperature; means for producing a temperature compensation signal which varies proportionally with detected environmental temperature; oscillator means for producing a d.c. voltage signal which is periodically discharged at a frequency ($f_1$) equal to a free running discharge frequency ($f_0$) of said oscillator means plus a compensation frequency ($f_c$) induced in said oscillator means by said temperature compensation signal; relative humidity sensor means which function as a frequency voltage converter to adjust a detected relative humidity signal produced by said relative humidity sensor means for changes in surrounding environmental temperature; means for producing said output signal which varies linearly with relative humidity in response to the adjusted relative humidity signal.

The present invention may also comprise, in accordance with its objects and purposes, a method of increasing the calibration period of a relative humidity sensor formed from an essentially pure layer of $Al_2O_3$ having a variable density gradient between a top and bottom electrode, said method comprising the steps of: generating a d.c. voltage signal; discharging said d.c. voltage signal to ground at a predetermined frequency with a discharge pulse width of approximately 60 μsec; applying said d.c. voltage signal to said relative humidity sensor as a biasing current.

The present invention may also comprise, in accordance with its objects and purposes, a relative humidity detector system for producing a substantially linear response to changes in relative humidity independent of changes in environmental temperature comprising: voltage controlled oscillator means for producing a d.c. output signal which is periodically discharged at a predetermined frequency; means for detecting environmental temperature; compensation means for producing a temperature compensation signal in response to said means for detecting; said compensation means attached to said voltage controlled oscillator means to vary said predetermined frequency proportionally with changes in environmental temperature; relative humidity sensor means for producing a detected relative humidity signal which varies in magnitude proportionally with detected relative humidity; means for applying said d.c. output signal to said relative humidity sensor means; said relative humidity sensor means functioning as a frequency to voltage converter to adjust said magnitude of said detected relative humidity signal by said temperature compensation signal to compensate for changes in response of said relative humidity sensor means due to changes in environmental temperature; output means connected to said relative humidity sensor means for providing a substantially linear relative humidity response independent of changes in environmental temperature.

The present invention may also comprise, in accordance with its objects and purposes, a relative humidity detector system for increasing the calibration period of a relative humidity sensor comprising: a relative humidity sensor formed from an essentially pure layer of $Al_2O_3$ having a variable density gradient between a top and bottom electrode; means for biasing said top electrode to maintain a substantially constant resistance across said top electrode and thereby maintain output sensitivity of said relative humidity sensor substantially constant.

The present invention may also comprise, in accordance with its objects and purposes, a relative humidity detector system for lengthening the calibration period of a relative humidity sensor comprising: a relative humidity sensor formed from an essentially pure layer of $Al_2O_3$ having a variable density gradient between a top and bottom electrode; and, means for biasing said top electrode with a predetermined current and voltage which remains substantially constant; whereby output sensitivity of said relative humidity sensor is maintained substantially constant by maintaining said predetermined current and voltage substantially constant.

OBJECTS OF THE INVENTION

It is therefore an object of the present invention to provide improved circuitry for implementing the improved sensor of the present invention.

It is also an object of the present invention to provide an improved relative humidity detector system.

Another object of the present invention is to provide a relative humidity detector system for producing a substantially linear response to changes in relative humidity independent of changes in environmental temperature.

Another object of the present invention is to provide a relative humidity detector system for increasing the calibration period of a relative humidity sensor.

Another object of the present invention is to provide a method of increasing the calibration period of the relative humidity sensor of the present invention.

Other objects, advantages and novel features of the present invention will become apparent from the following detailed description of the invention when considered in conjunction with the accompanying drawings wherein:

BRIEF DESCRIPTION OF THE DRAWINGS

FIG. 3b is a top view of the bottom electrode deposited on the device of FIG. 3a.

DETAILED DESCRIPTION OF THE PREFERRED EMBODIMENT OF THE INVENTION

Figure 1:
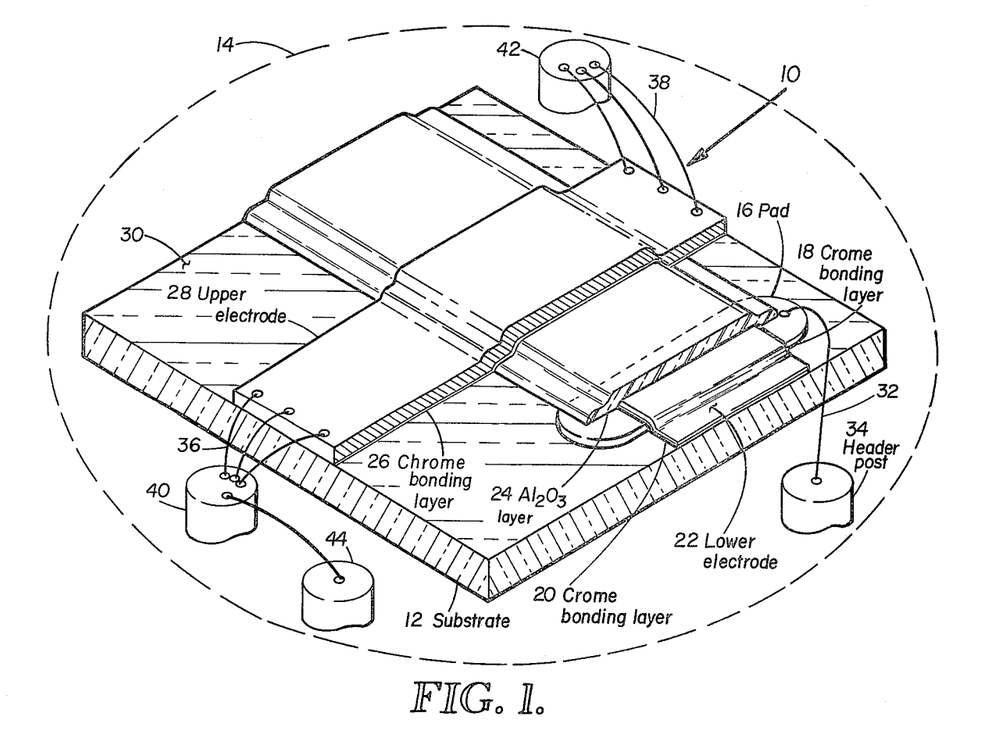
FIG. 1 is a perspective view of the sensor of the present invention.

FIG. 1 illustrates the sensor of the preferred embodiment of the present invention for detecting percentage, in the surrounding environment, of relative humidity. The device can also be used to simultaneously detect temperature utilizing the various circuitry disclosed herein.

Relative humidity sensors have a variety of utilities. For example, relative humidity sensors have been used for environmental control in grain silos, human habitat, computer rooms and military and commercial aircraft. They have also been used in automotive and aircraft systems for carburation control, rust studies, passenger environmental control, engine test cell monitoring, and to detect icing conditions on aircraft, highways, radar antennae, television broadcast antennae, turbines, etc. The sensors have also been used for moisture and leak detection in the NASA Space Shuttle engine, aircraft cooling systems, fuel tanks, sonar buoys, ammunition depot storage, torpedoes, waveguide transmission lines, hybrid circuits to test hermeticity, silo missile storage, heart pacemakers, gas-cooled reactors, and nuclear weapons. The sensors have additionally been used in humidity and temperature calibration systems in meteorology labs, sterilizers, film developing and calibration of radiosonde and dropsonde.

Referring again to FIG. 1, the sensor comprises a substrate 12 which is formed of quartz, amorphous glass or similar material. The particular choice of substrate material is not critical, but should be a material which is electrically insulating, and which has a relatively low temperature coefficient approximating that of subsequent layers to be deposited thereon, as described below. It has been found that amorphous quartz is particularly well suited for such use. A quartz substrate has been used in the present invention which measures 0.075"×0.070"×0.010", mounted on a standard header 14.

Deposited on substrate 12 is pad 16 formed from five nines pure gold or other noble metal having a thickness of approximately 10,000 Å, which overlies a chrome bonding layer 18 having a thickness of approximately 140 Å. Deposited over pad 16 is a chrome bonding layer 20 similar to chrome bonding layer 18. Lower electrode 22 is then deposited over chrome bonding layer 20. Lower electrode 22 is formed of five nines pure gold or other noble metal which is not affected by treatments in acid or base solutions.

Overlying the lower electrode 22 is a layer of essentially pure $Al_2O_3$ 24 which is substantially transparent, formed from a layer of Al metal having a thickness of approximately 120 Å to 5000 Å, according to the method of the preferred embodiment of the invention. As shown in FIG. 1, the $Al_2O_3$ layer extends beyond the edges of lower electrode 22 by approximately 2 to 4 mils to ensure electrical insulation of the lower electrode 22 from subsequently deposited layers. Chrome bonding layer 26 is deposited across the composite layers described above, such that layer 26 is deposited directly on the upper surface 30 of substrate 12 and upper surface of $Al_2O_3$ layer 24. Directly over chrome bonding layer 26 is deposited an upper electrode 28 of five nines pure gold or other suitable electrode material such as nickel, indium, or a noble metal, etc., depending upon the intended utilization of the electrode. The upper electrode 28, which is also referred to as the control electrode, has a thickness for gold ranging from approximately 7 Å to 1000 Å, limited in thinness by the conductivity of the metal and its ability to carry the requisite biasing currents, and in thickness by the porosity of the metal and its ability to pass water molecules to $Al_2O_3$ layer 24. The thickness for other metals such as nickel, indium, platinum, etc., of course, varies according to the characteristics of the metal and its ability to meet the above criteria. Since the upper electrode can also be used as a temperature sensor, which, when properly biased, exhibits a positive temperature coefficient in d.c. resistance, the thickness of the upper electrode and biasing current employed are design parameters which affect performance of the sensor depending upon its intended application.

Electrical connection to the lower electrode 22 is accomplished by attaching wire 32 between pad 16 and header post 34. To provided uniform distribution of biasing current, to spread the d.c. field through the $Al_2O_3$ layer 24 from the upper electrode 28, and to ensure that sufficient current can be carried, the plurality of wires 36 and 38 are attached evenly along the ends of upper electrode 28 to header posts 40 and 42, respectively. Each of the wires has a diameter of approximately 1-2 mils. Header post 44 is connected to header post 40 to act as a ground terminal or system common. Header post 42 is connected to the bias voltage while header post 34 functions as a signal terminal.

Figure 2:
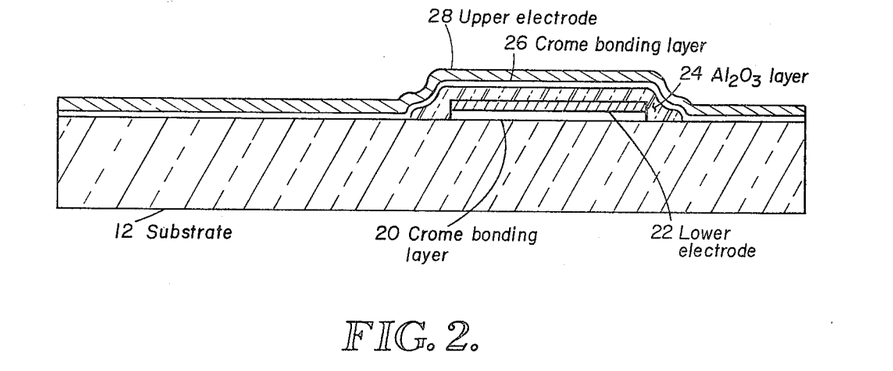
FIG. 2 is a cross-section of the sensor as shown in FIG. 3e.
Figure 3A:
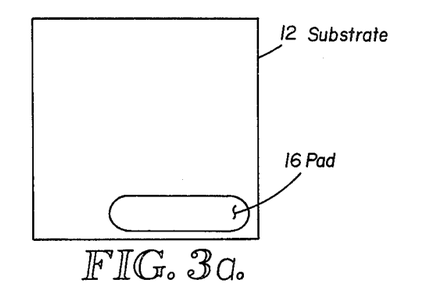
FIG. 3a is a top view of the substrate with a pad deposited thereon.
Figure 3B:
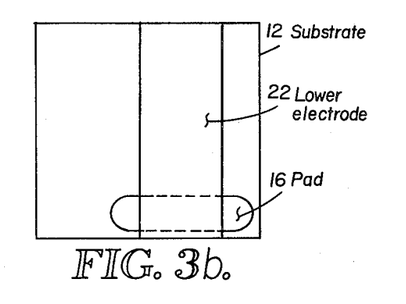
Figure 3C:
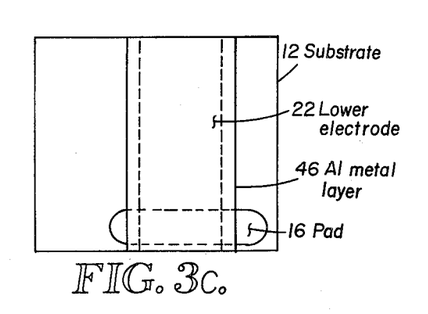
FIG. 3c is a top view of the Al metal layer deposited on the device of FIG. 3b.
Figure 3D:
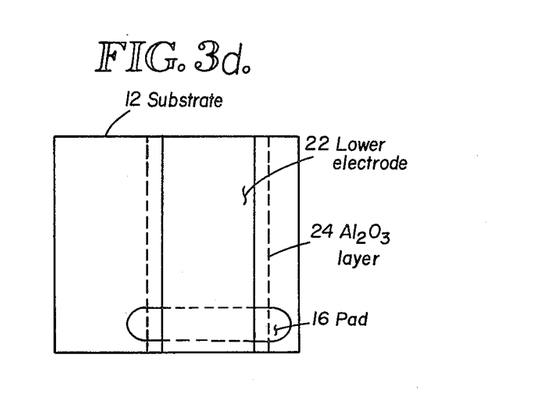
FIG. 3d is a top view of the device of FIG. 3c after the Al metal layer is anodized to form a layer of essentially pure $Al_2O_3$.
Figure 3E:
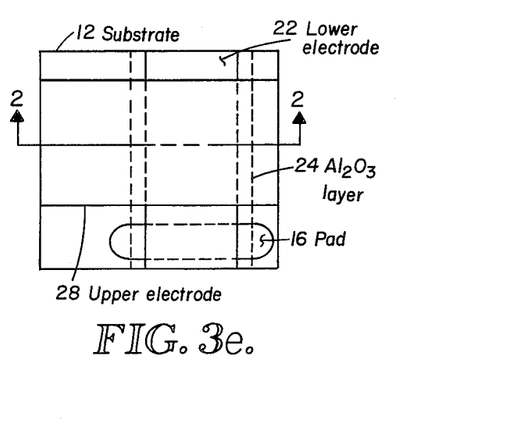
FIG. 3e is a top view of the final configuration showing the upper gold electrode deposited on the device of FIG. 3d.

FIG. 2 is a cross-sectional diagram of the sensor taken as shown in FIG. 3e. As in FIG. 1, the layers are shown schematically and are not drawn to scale. FIG. 2 illustrates the relationship of the various layers and substrate 12 to one another.

FIGS. 3a–3e illustrate the method of fabrication of the sensor of the present invention.

FIG. 3a is a top view of the substrate with pad 16 and chrome bonding layer 18 deposited thereon. The substrate 12 is freshly cleaved or sputtered prior to the deposition of the chrome bonding layer 18 to ensure bonding. The chrome layer 18 functions as a bonding layer for pad 16 on substrate 12. The chrome layer 18 is deposited to a thickness of approximately 140 Å while pad 16 is deposited directly over chrome bonding layer 18, without breaking vacuum, to a thickness of approximately 10,000 Å. The composite of FIG. 3a is then sputter cleaned for approximately two minutes to remove residual gas and impurities.

FIG. 3b illustrates the deposition of the lower electrode 22 formed from five nines pure gold, or other noble metal such as platinum, over the substrate 12 and upper surface of pad 16. Appropriate masking is used to deposit both chrome bonding layer 20 and lower electrode 22 without breaking vacuum. Again, the substrate should be freshly sputtered or cleaved to ensure bonding. The chrome layer 20 is approximately 140 Å thick while the lower electrode 22 is approximately 400 Å to 3000 Å thick.

The composite of FIG. 3 is then sputtered in a vacuum for approximately five minutes to roughen the pre-applied layers and to remove a number of angstroms from both the substrate 12 and layer interfaces, so as to provide a freshly cleaved surface to promote good adhesion of the finished semiconducting $Al_2O_3$ layer 24.

The composite is then masked for deposition of a layer 46 of five nines pure Al metal as shown in FIG. 3c. The Al metal layer 46 has a thickness ranging from 120

Å to 5000 Å depending upon final desired device characteristics. The Al metal layer 46 overlaps the lower electrode 22 by approximately 2-4 mils. The composite of FIG. 3c is then anodized in a particular manner in a special anodizing solution, as set forth below, to produce the novel and unique layer of essentially pure $Al_2O_3$ 24.

The anodizing solution is prepared in an optically clear container for visual observation purposes. The solution is prepared by mixing 17% by volume of 98% pure sulfuric acid with HPLC (purified) water. The solution prepared as set forth above, has a normality of approximately 6.4 gram equivalent weights/liter. While the solution is prepared in a particular manner as set forth above with sulfuric acid, other suitable methods of preparing the solution and even use of other suitable acids to obtain a freshly mixed solution having a normality of approximately 6.4 gram equivalent weights/liter, are acceptable.

The freshly mixed solution is then placed in a refrigeration unit and cooled to 18° C. Once cooled to 18° C., the solution is removed from the refrigeration unit and allowed to warm to approximately 21° C. in room temperature environment. The temperature of the solution rises naturally due to the continuing reaction taking place in the solution. It is important to note that some reaction must be taking place in the solution to obtain the desired results from the anodizing process.

The substrate is then connected to one side of a 60 Hz a.c. electrical signal while the other side is connected to a five nines pure aluminum electrode (anode). Once the solution reaches 21° C., the anode and substrate are placed in the solution with the deposited layers facing away from the anode. The voltage is carefully controlled to produce a 0.5 volt a.c. drop across a 10 ohm precision resistor placed in series with the anode.

The process is then viewed with a medium power stereo zoom microscope. The solution is not temperature controlled but the anodizing process should be performed in a room environment of approximately 20° C. Once the anodizing process starts, the solution will increase in temperature at a predetermined rate determined by the anodization process. The solution will normally increase 4-7° C. during the process which causes the layer of $Al_2O_3$ to have a density gradient which varies throughout the thickness of the $Al_2O_3$ layer from more dense on its upper surface to less dense at its lower surface. This density gradient is necessary to produce a substantially linear response to changes in relative humidity from 0% to 100% RH.

When viewing the anodization process through the microscope, bubble of gas are seen forming on the Al metal and releasing to go to the surface. The anodization process increases as the solution increases in temperature evidenced by rapidly accelerated bubbling. When bubbling is observed to decrease at a rapid rate and the lower electrode 22. becomes visible through the anodized layer, the composite is rapidly removed and disconnected from the a.c. electrical source and placed in HPLC water. The anodized layer should then be gently rinsed in HPLC water for 5 to 15 seconds.

Following a second rinse in HPLC water, the composite is placed, without drying, into a 10% solution of ammonium hydroxide for approximately 10 seconds. The ammonium hydroxide solution neutralizes and removes all traces of acid, residues of aluminum, and other impurities in the layer of $Al_2O_3$ 24 formed from the Al metal layer 46. Of course, other equivalent mixtures and/or bases can be used for the neutralization process as set forth above.

The $Al_2O_3$ layer 24 should then be rinsed thoroughly again in HPLC water, dipped into a clean rinse of HPLC water and plunged into a boiling solution of HPLC water for approximately 2 minutes. The composite should then be dipped into $CH_3CH(OH)CH_3$ to remove excess $H_2O$, followed by two separate dips in fresh $CH_3CH(OH)CH_3$. The composite is then dried in a filtered stream of nitrogen.

Upon observation of the composite, no $Al_2O_3$ layer is visible with the naked eye or under a low-power microscope. However, under higher power, the substantially transparent layer of $Al_2O_3$ 24 is visible.

This is more clearly shown in FIG. 3d where $Al_2O_3$ layer 24 is essentially transparent such that the lower electrode 22 is clearly visible. By following the above process, the essentially pure layer of $Al_2O_3$ is approximately the same thickness as the original Al metal layer 46.

The composite of FIG. 3d is then placed in a clean, covered, petri dish and placed in a dry oven at 105° C. for 24 hours. This step anneals the $Al_2O_3$ layer to the lower electrode 22 and substrate 12 to prevent crazing, cracking and peeling during final processing.

Following the annealing process, the composite is place immediately in a vacuum for deposition of additional layers of the sensor 10. Pump-down should be instituted as soon as possible and continued until $10^{-6}$ torr is obtained. A chrome bonding layer 26 is then deposited to a thickness of approximately 140 Å, followed by deposition of the upper electrode 28 to a total thickness of approximately 400 Å including the chrome layer 26, in a configuration as shown in FIG. 3e and FIG. 1.

Following pump-down, the sensor illustrated in FIG. 3e is placed in a covered petri dish and placed in a dry oven at 125° C. for 72 hours. Heat treating, in this manner, anneals the composite sensor to prevent peeling, crazing, cracking, etc., as set forth above. The sensor may then be left at ambient temperature until divided into individual sensors.

Although FIGS. 3a-3e illustrate the above process as fabrication of a single sensor, in actuality a number of sensors are fabricated simultaneously by depositing long strips of the various layers in a patchwork pattern on a larger substrate. The larger substrate is then divided into a plurality of smaller, single sensors illustrated in FIG. 1 and 3e.

The individual sensors are then mounted on the desired header and electrically connected to header posts and packaged in the desired manner for the intended use. Of course, the sensor can be packaged directly with the processing integrated circuitry due to its size and ability to be operated with d.c. biasing.

Auger analysis of the $Al_2O_3$ layer formed according to the disclosed method reveals no detectable Al metal present. Microscopic inspection of the essentially pure $Al_2O_3$ layer reveals a disordered crystalline structure with very short pores penetrating the upper surface, or no pores at all. The upper region of the $Al_2O_3$ layer, which was anodized in a cooler acid solution, is denser than lower regions which were anodized in a higher temperature acid solution at a more rapid rate. The density of the essentially pure $Al_2O_3$ layer consequently forms a density gradient which increases progressively from the upper surface to the lower surface. This provides a linear response of the sensor for the complete range of relative humidities from 0% to 100%

RH. The neutralization of acid and removal of impurities using the base solution additionally ensures that the sensor will not be subject to progressive aging.

Figure 4:
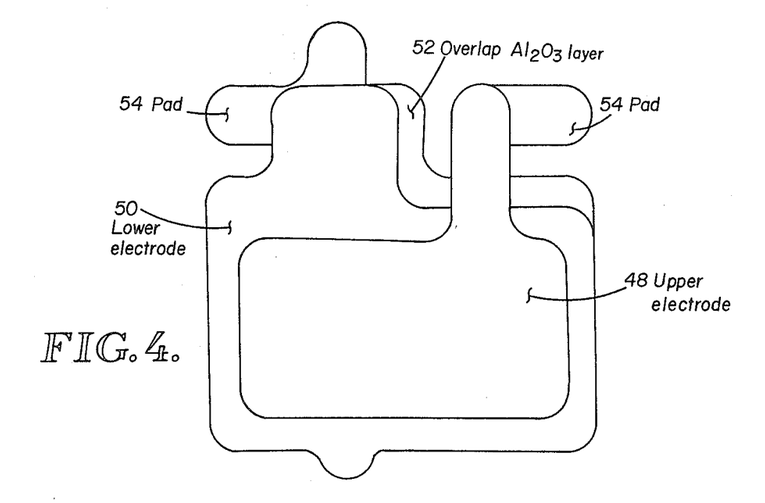
FIG. 4 is an alternative sensor configuration.

FIG. 4 illustrates an alternative arrangement of layers to produce a sensor in accordance with the preferred embodiment of the invention. The sensor portion comprises an upper electrode 48, lower electrode 50, and an Al₂O₃ layer 52. Pads 54 and 56 function as electrical connectors to the electrodes. Additionally, electrical wires can be connected directly to upper electrode 48.

Figure 5:
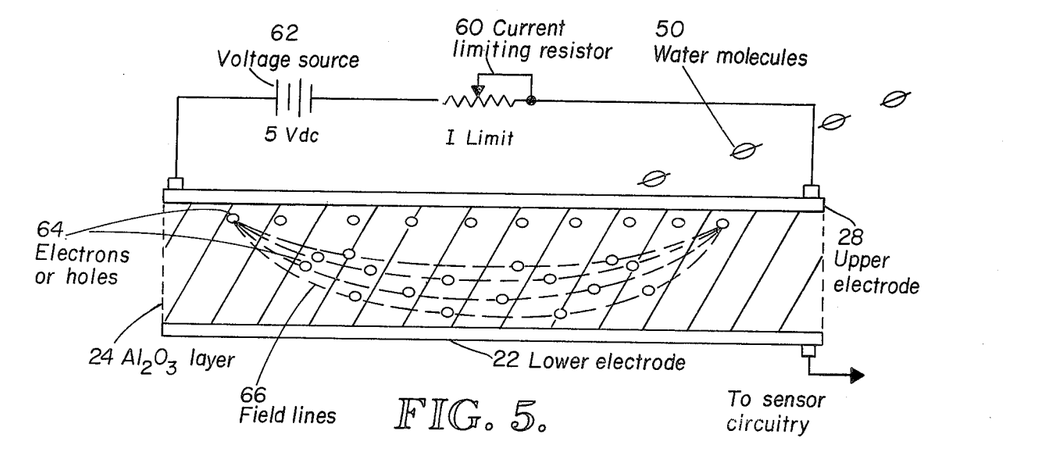
FIG. 5 is a schematic diagram of a biased sensor illustrating the effect of biasing.

FIG. 5 is a schematic diagram illustrating the manner in which the sensor 10 of the present invention may be used as a three terminal device. As opposed to prior art sensors which are used as capacitors in conjunction with an alternating current signal to detect changes in humidity, the present invention uses a d.c. bias signal provided by voltage source 62 and current limiting resistor 60 to operate the sensor as a semiconductor device. The bias provided on the control electrode or upper electrode 28, as shown in FIG. 5, generates a fixed field in the Al₂O₃ semiconducting layer 24 shown by field lines 66. The field lines prevent the movement of dipoles (water molecules) through Al₂O₃ layer 24 at different energy levels. Energy from water molecules 50 which have an energy level determined by their temperature, penetrate the upper electrode 28 and Al₂O₃ layer 24 causing the Al₂O₃ layer to conduct more or less depending upon the density of water molecules 50 and their thermal energy.

Figure 6:
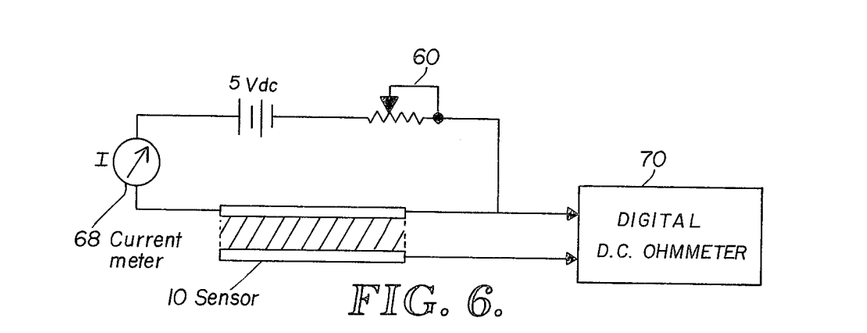
FIG. 6 is a test circuit for measuring series d.c. resistance change of the $Al_2O_3$ layer with changing bias control current.
Figure 7:
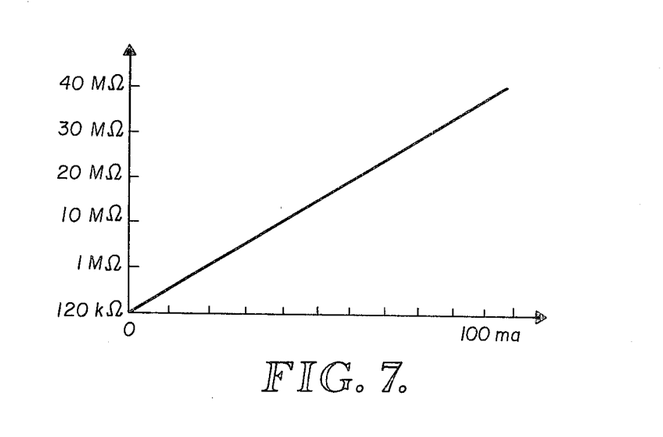
FIG. 7 is a graph of resistance in ohms vs. current in milliamps illustrating the series d.c. resistance change of the $Al_2O_3$ layer with changing bias control current, as measured by the device of FIG. 6.

FIGS. 6 and 7 illustrate the series d.c. resistance measured between the upper electrode 28 and lower electrode 22 for various currents applied to upper electrode 28. A gating or blocking effect is produced in the sensor 10 that causes the series d.c. resistance measured by ohmmeter 70 to vary linearly with the amount of biasing current applied, as measured by current meter 68 and controlled by current limiting resistor 60.

A typical response for a detector produced in accordance with the prevent invention is graphically illustrated in FIG. 7. As shown, currents of a few milliamps will cause the series d.c. resistance of the sensor to increase by several megaohms. Currents of 100 ma to 200 ma produce heating in the device and increase the series d.c. resistance several orders of magnitude. As shown in FIG. 7, currents as low as 1 ma are sufficient to bias the sensor for operation as a three-terminal device which provides a linear response to changes in relative humidity.

In the course of development of the present invention, d.c. ohmic measurements were made across the length of upper electrode 28 which was found to display a resistance, end to end, of approximately 4.5 ohms to 5.5 ohms or slightly higher. It was also found that the upper electrode 28 displays a positive linear resistance coefficient with changes in temperature of the sensor which is not affected by changes in humidity. Sensor 10 can therefore be operated as a temperature sensor and a relative humidity sensor simultaneously.

Figure 8:
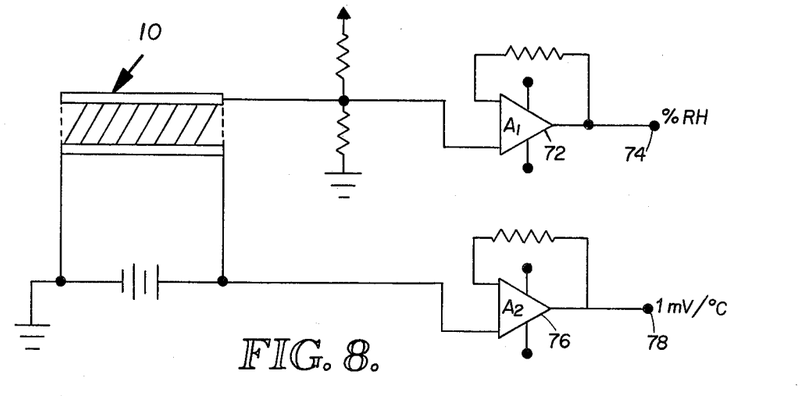
FIG. 8 is a schematic diagram of a circuit arrangement for measuring both percentage of relative humidity and temperature from a single sensor.
Figure 9:
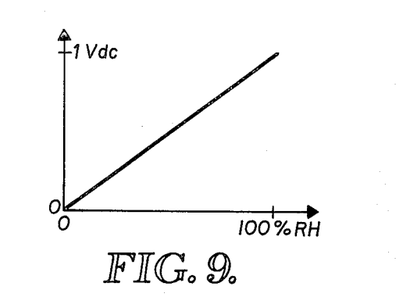
FIG. 9 is a graph illustrating results of detected percentage of relative humidity from the circuit of FIG. 8.

FIG. 8 is a schematic diagram of a typical circuit for operating sensor 10 as both a temperature sensor and relative humidity sensor. Amplifier (A₁) 72 is adjusted to produce 1 millivolt/%RH at output 74 so that 1 volt d.c. is equivalent to 100% RH. A typical linear response of sensor 10 produced at output 74 is illustrated in FIG. 9.

Figure 10:
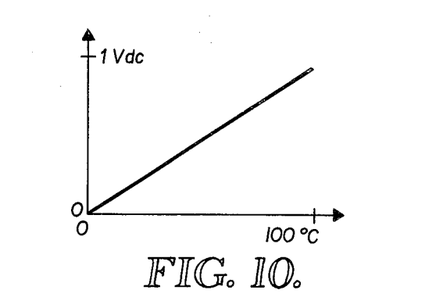
FIG. 10 is a graph illustrating results of detected temperature from the circuit of FIG. 8.

Amplifier (A₂) 76 is adjusted to produce 1 millivolt/°C. so that output 78 produces outputs which vary between zero volts d.c. and 1 volts d.c., representing changes from 0° C. to 100° C., as shown in FIG. 10.

Figure 11:
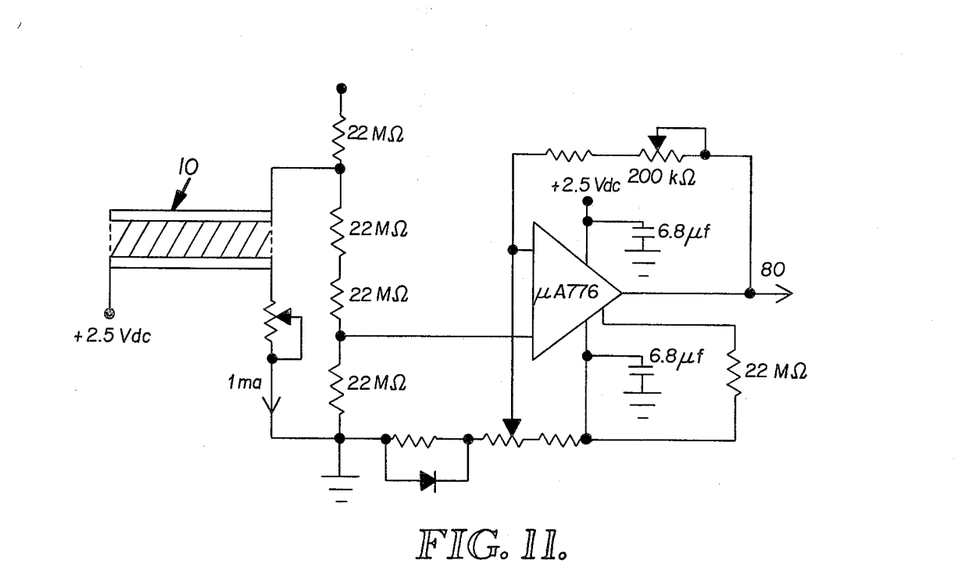
FIG. 11 is a schematic diagram of a particular low current d.c. amplification circuit.

A particular amplification configuration to detect relative humidity is schematically illustrated in FIG. 11. With proper biasing of the sensor, the voltage at output 80 varies between 0-1 V d.c. to indicate changes in humidity of 0%-100% RH.

The sensor of the present invention is therefore capable of detecting changes in RH in a linear manner between 0% to 100% RH. The linear response of the sensor 10 is a result of the disordered crystalline structure of the essentially pure Al₂O₃ layer which has a density gradient which varies from denser to less dense from its upper surface to its lower surface. The particular method of fabrication, i.e., utilizing a particular starting temperature, e.g. 21° C., and allowing the temperature to rise at its own rate during the anodization process, gives rise to the disordered crystalline structure and density gradient which allows the sensor 10 to operate in a linear manner in response to changes in RH.

The sensor can also simultaneously function as a temperature sensor further increasing its utility for application where both relative humidity and temperature are desired. Among other applications, this is particularly useful for detecting icing conditions. Neutralization and removal of impurities from essentially pure Al₂O₃ layer also prevents progressive periodic recalibration resulting from progressive aging.

Figures 12, 13:
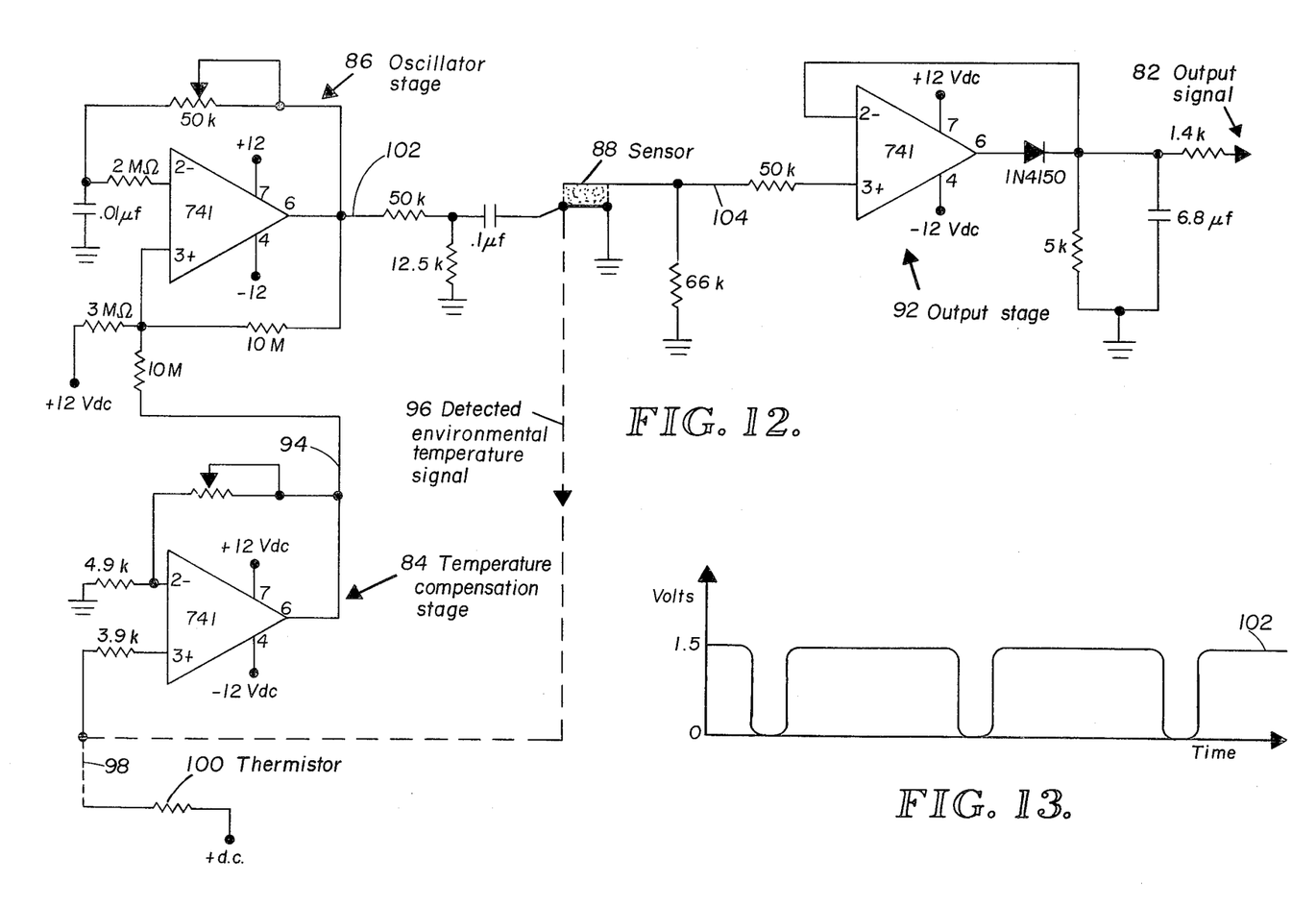
FIG. 12 is a schematic diagram of a relative humidity detector system in accordance with the present invention for compensating for changes in sensitivity of the relative humidity sensor due to changes in environmental temperature.
FIG. 13 is a graph (not to scale) of a typical d.c. output signal which is discharged at a predetermined frequency produced by the oscillator stage illustrated in FIG. 12 in accordance with the present invention.

However, changes in environmental temperature affect the relative humidity response of the sensor as pointed out in the Background of the Invention. Moreover, a constant biasing current across the sensor has resulted in progressive aging as detected in sensor response after extended periods of use of the sensor. FIG. 12 discloses a relative humidity detector system for overcoming these problems resulting from changes in environmental temperature and progressive aging. The relative humidity detector system of FIG. 12 comprises a temperature compensation stage 84, an oscillator stage 86, the sensor 88 of the present invention with associated circuitry, and output stage 92.

Temperature compensation stage 84 produces a temperature compensation signal 94 representative of detected environmental temperature, i.e. the temperature of the medium surrounding the relative humidity detector system. A detected environmental temperature signal is produced by an appropriately biased sensor 88, such as disclosed above in FIG. 8 or by a thermistor 100, such as disclosed in FIG. 12.

The temperature compensation signal 94 is applied to oscillator stage 86 to adjust the output of oscillator stage 86. Oscillator stage 86 produces a d.c. output signal 102 which is periodically discharged to ground (zero volts) at a frequency ($f_l$), such as illustrated in FIG. 13. Temperature compensation signal 94 adjusts the free running, discharge frequency which is set at a predetermined discharge frequency ($f_o$) such as, for example, 4.3 KHz, of the oscillator stage 86 by a compensation frequency ($f_c$) induced in the oscillator stage 86 by the temperature compensation signal 94. In this manner, oscillator stage 86 functions as a voltage controlled oscillator by producing a periodically discharged d.c. output signal having a discharge frequency which is adjusted by the voltage magnitude of temperature compensation signal 94.

The periodically discharged d.c. output signal 102, illustrated in FIG. 13, functions both as a frequency source and a biasing source for sensor 88. The exemplary d.c. level of 1.5 volts, illustrated in FIG. 13, provides a biasing current through the top electrode of sensor 88 to provide the various advantages set forth above. Periodic discharge, in the manner illustrated in FIG. 13, has been found to increase the calibration period (time between calibration) of the relative humidity detector system when compared to constant biasing of the sensor.

Figure 14:
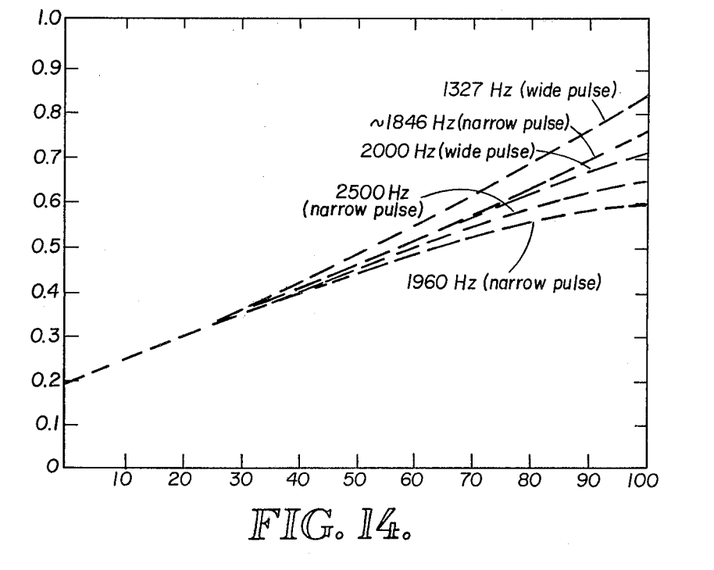
FIG. 14 is a graph of the response (ordinate) of the sensor of the present invention for various relative humidities (axis).
Figure 15:
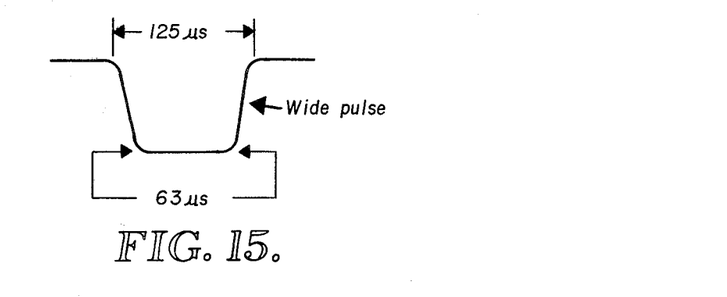
FIG. 15 is a schematic diagram of the wide pulse used in the graph of FIG. 14.

As illustrated in FIG. 14, various responses are shown for various discharge frequencies and two different pulse widths. The narrow pulse referred to in FIG. 14 is a short pulse approximating an impulse when compared to the wide pulse illustrated in FIG. 15. The wide pulse of FIG. 15, having an approximately 60 $\mu$s pulse width, produced the best results as illustrated in FIG. 14 showing minimal "roll over" at lower discharge frequencies, when compared to the short pulse.

The sensor 88 also functions as a substantially linear frequency to voltage converter. The linear frequency to voltage conversion characteristics of sensor 88, fabricated in accordance with the present invention, allows for compensation of output sensitivity of the sensor for changes in environmental temperature. It has been found that the detected relative humidity of the sensor of the present invention varies slightly with changes in environmental temperature, as set forth above. In order to obtain a corrected reading of relative humidity for changing environmental temperature situations, it is necessary to adjust the detected relative humidity of the sensor by a temperature compensation factor in the manner illustrated in FIG. 12. The frequency to voltage conversion characteristics of sensor 88 are used in conjunction with the advantageous effects of periodic discharge of the biasing current in the system of FIG. 12 to vary the discharge frequency of the d.c. biasing signal to adjust the voltage output of the sensor 88 to compensate for changes in sensitivity of the sensor due to changes in environmental temperature. In this manner, an adjusted relative humidity signal is produced representative of a true reading of relative humidity.

Figure 16:
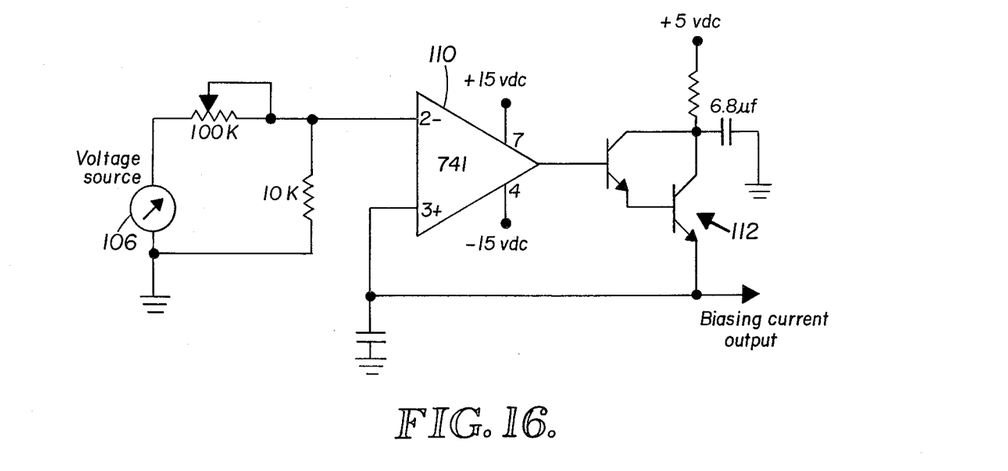
FIG. 16 is a biasing circuit for maintaining a substantially constant output sensitivity from the relative humidity sensor.

FIG. 16 illustrates an alternative biasing circuit which can be used where the sensor of the present invention is employed in high environmental temperature surroundings, e.g. 50° C. or more. Voltage source 106 produces a reference voltage which is maintained by the circuit of FIG. 16 across the top electrode of the sensor. Potentiometer 108 is used to set a desired biasing current which is maintained by operational amplifier 110 and darlington pair 112. For high environmental temperature applications, where top electrode resistance attempts to change due to more rapid aging resulting from the higher temperatures, the biasing circuit of FIG. 16 maintains a substantially constant resistance across the top electrode to lengthen the calibration period. Of course, the circuit of FIG. 16 can be used at any temperature and can also be employed in the relative humidity detection system illustrated in FIG. 12 to further increase the calibration period.

In addition to the above disclosed methods and devices for lengthening calibration period of the sensor, adjusting output response for changes in sensitivity of the sensor for changing environmental temperatures, and adjusting linearity of the sensor by various methods during fabrication and subsequent implementation in various biasing circuits, it should be pointed out that since the novel and unique sensor of the present invention is a three terminal semiconductor device, the internal resistance between the top and bottom electrodes can be changed by changing the biasing current. This allows implementation of the sensor to match a particular circuit or requirement. For example, the sensor of the present invention can be biased to detect true moisture level rather than relative humidity for detection of, for example, soil moisture levels or moisture levels in drying concrete.

Additionally, the sensor can be biased at several different levels to determine its most linear relative humidity response to ensure the best available response for each particular sensor.

The present invention therefore provides relative humidity detector systems for producing substantially linear responses to changes in relative humidity, independent of changes in environmental temperature, and methods and devices for increasing the calibration period of the sensor of the present invention.

Obviously, many modifications and variations of the present invention are possible in light of the above teachings. For example, the particular configuration of the sensor is not critical to its operation. Configurations other than those specifically shown in FIGS. 1 and 4 can be used in an equivalent manner. Moreover, the sensor can be used in any desired packaging arrangement, depending upon the intended use of the device. It is therefore to be understood that within the scope of the appended claims, the invention may be practiced otherwise than as specifically described, and that subject matter disclosed herein shall not be precluded from being later claimed in the present application, or a continuation, continuation-in-part, or reissue application.

What is claimed is:

1. A relative humidity detector system for generating an output signal which varies linearly with relative humidity, essentially independent of changes in surrounding environmental temperature, comprising:
    means for detecting surrounding environmental temperature;
    means for producing a temperature compensation signal which varies proportionally with detected environmental temperature;
    oscillator means for producing a d.c. voltage signal which is periodically discharged at a frequency ($f_j$) equal to a free running discharge frequency ($f_o$) of said oscillator means plus a compensation frequency ($f_c$) induced in said oscillator means by said temperature compensation signal;
    relative humidity sensor means for producing a detected relative humidity signal, said relative humidity sensor means connected to said oscillator means such that said relative humidity sensor means functions as a frequency to voltage converter to adjust said detected relative humidity signal for changes in surrounding environmental temperature proportionally with said frequency ($f_j$);
    means for producing said output signal which varies linearly with relative humidity in response to the adjusted relative humidity signal.

2. The system of claim 1 wherein said means for detecting surrounding environmental temperature comprises a thermistor.

3. The system of claim 1 wherein said means for detecting surrounding environmental temperature comprises said relative humidity sensor means.

4. The system of claim 1 wherein said relative humidity sensor means is formed from an essentially pure layer of $Al_2O_3$ having a variable density gradient.

5. A relative humidity detector system for producing a substantially linear response to changes in relative humidity independent of changes in environmental temperature comprising:

voltage controlled oscillator means for producing a d.c. output signal which is periodically discharged at a predetermined frequency;

means for detecting environmental temperature;

compensation means for producing a temperature compensation signal in response to said means for detecting, said compensation means attached to said voltage controlled oscillator means to vary said predetermined frequency proportionally with changes in environmental temperature;

relative humidity sensor means for producing a detected relative humidity signal which varies in magnitude proportionally with detected relative humidity;

means for applying said d.c. output signal to said relative humidity sensor means, said relative humidity sensor means functioning as a frequency to voltage converter to adjust said magnitude of said detected relative humidity signal by said temperature compensation signal to compensate for changes in response of said relative humidity sensor means due to changes in environmental temperature;

output means connected to said relative humidity sensor means for providing a substantially linear relative humidity response independent of changes in environmental temperature.

6. The system of claim 5 wherein said relative humidity sensor means is formed from an essentially pure layer of $Al_2O_3$ having a variable density gradient.

7. The system of claim 5 wherein said means for detecting surrounding environmental temperature comprises a thermistor.

8. The system of claim 5 wherein said means for detecting surrounding environmental temperature comprises said relative humidity sensor means.

9. A relative humidity detector system for increasing the calibration period of a relative humidity sensor comprising:

a relative humidity sensor formed from an essentially pure layer of $Al_2O_3$ having a variable density gradient between a top and bottom electrode;

means for biasing said top electrode to maintain a substantially constant resistance across said top electrode and thereby maintain output sensitivity of said relative humidity sensor substantially constant.

10. A relative humidity detector system for lengthening the calibration period of a relative humidity sensor comprising:

a relative humidity sensor formed from an essentially pure layer of $Al_2O_3$ having a variable density gradient between a top and bottom electrode; and, means for biasing said top electrode with a predetermined current and voltage which remains substantially constant;

whereby output sensitivity of said relative humidity sensor is maintained substantially constant by maintaining said predetermined current and voltage substantially constant.

11. A method of increasing the calibration period of a relative humidity sensor formed from an essentially pure layer of $Al_2O_3$ having a variable density gradient between a top and bottom electrode, said method comprising the steps of:

generating a d.c. voltage signal;

discharging said d.c. voltage signal to ground at a predetermined frequency with a discharge pulse width of approximately 60 $\mu$sec;

applying said d.c. voltage signal to said relative humidity sensor as a biasing voltage.

* * * * *